United States Patent [19]

Wright et al.

[11] 4,348,635

[45] Sep. 7, 1982

[54] DETECTING AND MEASURING THE POSITION OF A BREAK IN SOLID FORMATIONS BY MEASURING THE CAPACITANCE OF AN ENLONGATED ELEMENT EMBEDDED THEREIN

[75] Inventors: David Wright, Vershire, Vt.; Ivor Hawkes, Hanover, N.H.

[73] Assignee: Joy Manufacturing Company, Pittsburgh, Pa.

[21] Appl. No.: 97,107

[22] Filed: Nov. 23, 1979

Related U.S. Application Data

[63] Continuation of Ser. No. 867,393, Jan. 6, 1978, abandoned.

[51] Int. Cl.³ .................... G01B 7/22; G01R 31/08; G01L 1/14
[52] U.S. Cl. ........................... 324/52; 73/784; 324/61 R; 340/690
[58] Field of Search .......... 324/52, 61 R, 61 P, 52, 324/51, 326; 73/762, 768, 594, 775, 595, 780, 781, 784, 799, 803; 340/690, 564, 563, 562; 361/280, 283, 324

[56] References Cited

U.S. PATENT DOCUMENTS

| | | | |
|---|---|---|---|
| 2,614,416 | 10/1952 | Hollmann | 324/61 P |
| 3,015,950 | 1/1962 | Doctor et al. | 324/61 R X |
| 3,175,527 | 3/1965 | Deaner | 324/61 R X |
| 3,284,704 | 11/1966 | Lamont | 324/52 |
| 3,400,331 | 9/1968 | Harris | 324/61 P |
| 3,409,886 | 11/1968 | Davis et al. | |
| 3,477,019 | 11/1969 | Hartmann | 324/52 X |
| 3,509,942 | 5/1970 | Lindberg | 73/781 X |
| 3,588,689 | 6/1971 | Crawford | 324/52 |
| 3,596,269 | 7/1971 | Laska | 324/51 X |
| 3,633,533 | 1/1972 | Allen et al. | 324/326 X |
| 3,634,845 | 1/1972 | Coleman | |
| 3,909,331 | 9/1975 | Cohen | |
| 4,029,889 | 6/1977 | Mizuochi | 324/52 X |
| 4,041,771 | 8/1977 | Allan et al. | 324/52 X |
| 4,095,174 | 6/1978 | Ishido | 324/61 R X |

*Primary Examiner*—Gerard R. Strecker
*Attorney, Agent, or Firm*—Ernest E. Helms

[57] ABSTRACT

This invention relates to an apparatus and method for detecting and measuring the position of a fracture in solid formations, such as for example a grout filled borehole. An electrical element is placed the length of the borehole prior to filling the hole with grout. When the hole is filled and the grout solidified, any fracture in the grout also breaks the electrical element. The element is constructed such that its electrical capacitance is a known function of its length. The element is constructed of easily frangible materials so that it is severed in close proximity to the grout fracture. The capacitance of the element after the fracture can be measured using suitable instrumentation. The position of the break is a function of the capacitance as measured after the break.

11 Claims, 10 Drawing Figures

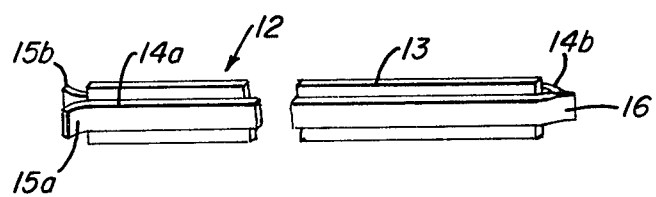
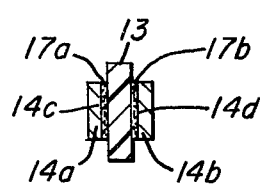
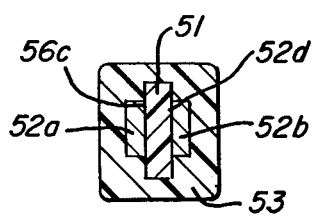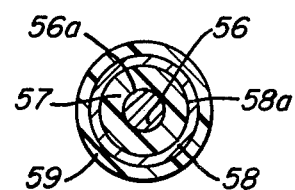
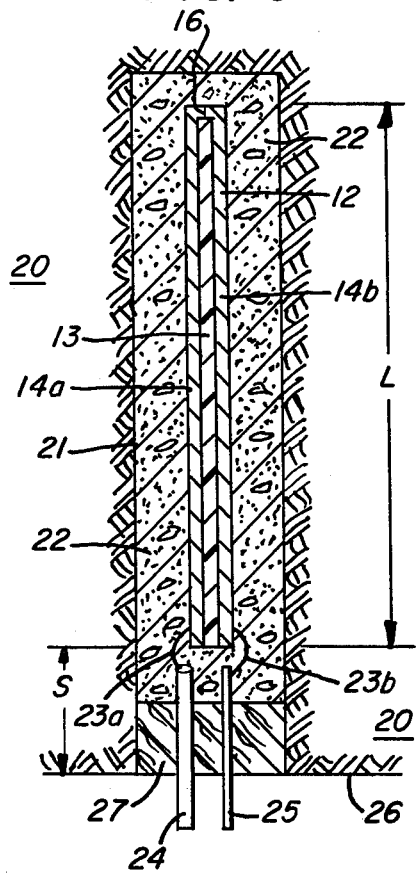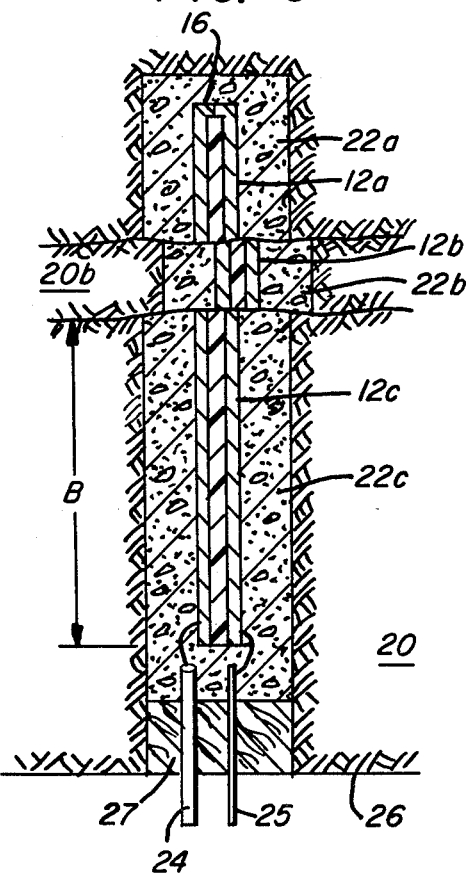

DETECTING AND MEASURING THE POSITION OF A BREAK IN SOLID FORMATIONS BY MEASURING THE CAPACITANCE OF AN ENLONGATED ELEMENT EMBEDDED THEREIN

This is a continuation, of application Ser. No. 867,393, filed Jan. 6, 1978, now abandoned.

BACKGROUND OF THE INVENTION

In many applications involving large solid structures it is desirable to detect internal disturbances. It is additionally valuable to be able to measure the position of such disturbances without further disturbing the integrity of the structure. In mining and construction it is often required to detect faults or disturbances and their positions in earth and rock formations. To detect such faults an electrical element can rigidly be embedded into the solid structure or earth. When a portion of the solid breaks or moves relative to the electrical elements it causes the electrical element to shear or break. Prior methods have used a ladder like arrangement of parallel resistors as taught by U.S. Pat. No. 3,477,019. Such systems lack accuracy because of their use of discrete components. The accuracy of such system is directly proportional to the number of components and cost. Because these devices determine position by measuring resistance between parallel conductors, any shunting resistance such as moisture paths between the conductors results in an error in position determination. My invention overcomes these inherent faults by using capacitance as a measure of position and by using one continuous inexpensive element.

An elongated electrical element is embedded in a solid formation. This element is made of easily shearable materials and has a capacitance that varies as a function of length. The element acts as an end-feed capacitor having accessible leads attached to the conductive surfaces at one end of the elongated element. When a meaningful disturbance occurs in the formation the frangible element breaks in the area of the disturbance effectively severing the element into at least two lengths and reducing the effective capacitance connected to the leads. The position of the break can be determined by measuring the capacitance at the leads and relating it to the length by the previously known function.

It is often required to know the position of a disturbance in a solid formation such as earth, rock, or formed conglomerates. This information is especially valuable in excavations such as are found in mining and construction for example. In such applications boreholes are normally drilled to test or reinforce the strata or solids. In one application of my invention an elongated electrical element is securely embedded generally axially within these boreholes. The electrical element does not interfere with other objects such as for example, structural rods or bolts that may be included within the same borehole. A hard cementitous material such as for example concrete can be used to embed the electrical element within the borehole. If it is desired to detect a very slight earth movement or no additional strengthening of the earth formation is required, a weaker, more brittle material can be used as the embedding grout. The grout used need only be capable of transmitting the movement or force of the disturbance in sufficient amount to shear or break the electrical element. The electrical element is made of frangible materials that are easily severed by the forces present during a detectable disturbance. Firmly grouting the electrical element into the solid and constructing the element from easily shearable material, causes the element to sever at a point corresponding to the location of a disturbance or movement in the solid.

The point at which the electrical element is severed can be calculated by comparing the electrical characteristics before the disturbance with those after. The electrical element is constructed so that the electrical characteristics are of a known function of the physical length of the elongated element. While any known function is sufficient, it will be desirable to use a continuous linear function so as to simplify the calculations. In certain applications it may be desirable to use a non-linear function which better suits the physical parameters of the disturbance; such as designing the element so that the electrical characteristics vary greater per unit length in the area where disturbances are anticipated so that the highest resolution and accuracy will be obtained in that area.

Variation in the capacitance for non-linear elements may be made by varying the distance between electrical conductive surfaces, increasing or decreasing the area of the electrical conductive surface, or using electrical insulating material of varying dielectric constants between the conductive surfaces.

If the elongated element is constructed to have a capacitance which is a linear function of the elongation, such as a parallel plate capacitor; then the position of the disturbance is directly proportional to the capacitance measured at the exposed leads. Additionally, the ends of the capacitor plates opposite the exposed leads can be shorted together to allow a continuity check from the exposed leads. A positive continuity check indicates an unbroken capacitor and no further capacitance measurement need be taken.

Accordingly, one object of this invention is to provide a means to accurately and economically determine the position of a movement within a solid formation.

Another object is to provide for the detection of breaks in the grout material as a function of the elongated frangible element.

Another object is to provide an inexpensive electrical element that can readily be inserted into a borehole and easily fashioned to the exact depth of the borehole.

Additional objects and features of the present invention will become apparent to those skilled in the art as the following description of certain present preferred embodiments thereof proceeds.

DRAWING DESCRIPTION

In the accompanying drawings are shown present preferred embodiments and methods of practicing the same in which:

FIG. 1 is a perspective view of an elongated element using foil conductive surfaces and a strip dielectric, having the foils shorted on one end;

FIG. 2 is a cross-sectional view taken transverse to the elongated direction of an element similar to that shown in FIG. 1;

FIG. 3 is a cross-sectional view of an element similar to that of FIG. 2 except having an outer insulating covering;

FIG. 4 is a cross-section view of an element using a coaxial arrangement of conducting surfaces and an outer insulating covering;

FIG. 5 is a cross-sectional view of a borehole, such as in a mine roof showing an element embedded in grout;

FIG. 6 is similar to FIG. 5 but shows a disturbance and resulting fracture of the electrical element occuring at a distance B from the connecting end of the element;

Figure 7:
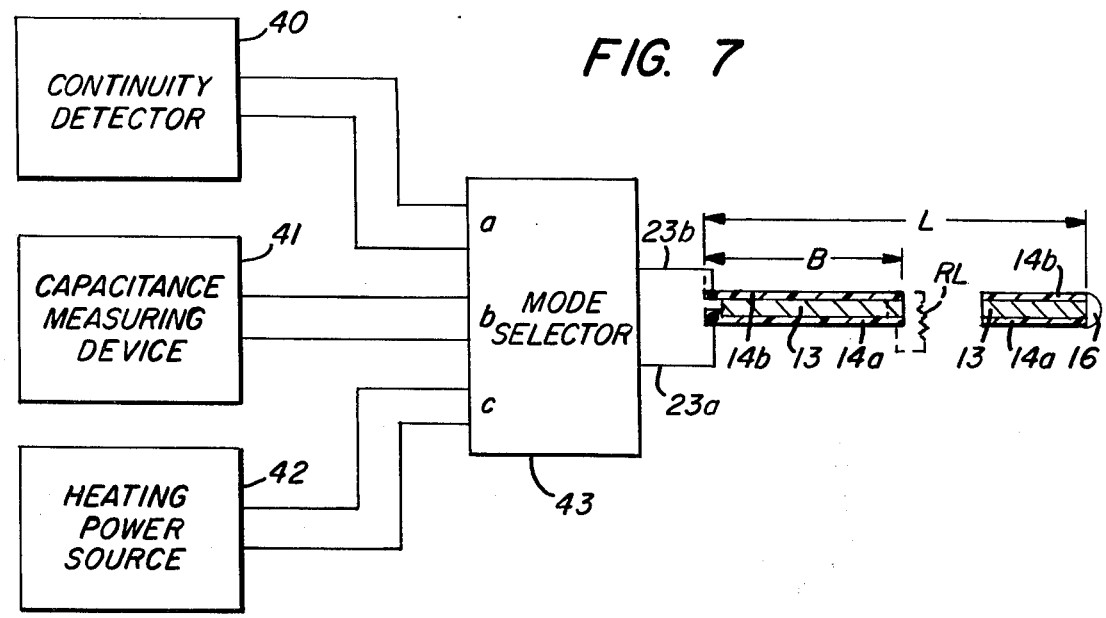
FIG. 7 is a schematic block diagram showing the apparatus and modes for determining the position of a break.

Shown in FIG. 1 is an embodiment of a parallel plate element that uses the characteristics of capacitance and continuity to detect a fault and determine the position of the disturbance. The element generally indicated by the reference 12, has been drawn broken to effectively show both ends of the elongated element. The element 12 can be of any length from a few feet to several hundred feet. The center portion of this element is composed of a dielectric strip or tape 13 which generally extends the length of the element. This dielectric strip may be, for example, a paper or plastic tape. While a dielectric material of any thickness will function in forming a capacitance in this parallel plate element, a 3 mil thick tape will tend to create a reasonable capacitance per linear foot of the elongated element and allow the element to be flexible during storage prior to installation.

Firmly attached to each side of the dielectric strip 13 are parallel electrically conductive means or foils, 14a and 14b for storing electrical charge. The conductive foil strips or commonly referred to as tapes 14a and 14b have respective conducting surfaces 14c and 14d abutting the dielectric strip 13. The conductive foils and respective conducting surfaces are held in fixed relationship to the dielectric strip 13 by adhesive layers 17a, 17b.

The conductive foils 14a and 14b can be made of any electrically conductive material that is frangible when subjected to the forces present in the particular disturbance desired to be detected. The conductive foil is made so as to sever generally transverse to the length of the element in close proximity to differences in forces along its length. These forces may be caused for example by a displacement in the grouting material resulting from a shift or fault movement in the solid. While only one conductive foil need be frangible it will usually be desirable to have both conductive foils made of similar materials.

At one end of the element corresponding for example to the maximum depth in a borehole installation, the conductive foils 14a and 14b are electrically connected by shorting means, for example, shorting fold 16. While any means for electrically connecting these two conductive foils may be used, such as wiring, stapling or mechanically joining, it has been found that removing a portion of the dielectric allows one conductive foil strip such as 14a, to be folded on the other conductive foil strip such as 14b.

At the end of the element 12 opposite the shorting fold 16, the two conductive foils 14a and 14b have been extended to produce connecting ends 15a and 15b, respectively. These connecting ends 15a and 15b can be either directly connected to electrical instrumentation or connected to other conductors or terminals that provide for connection to electrical devices. In other embodiments provision can be made for connecting wires or terminals directly to the ends of foils 14a and 14b without extending the foils. In such embodiments, the object is to provide connective means for the respective ends of the conductive surfaces. This allows the conductive surfaces to be electrically charged or discharged through the connective means into instrumentation which measures the capacitance of the element. Such connective means also allows a test of the continuity through the path of series connected conductive foils 14a, shorting fold 16 and conductive foil 14b.

FIG. 2 is a cross-section, of a parallel plate element similar to that shown in FIG. 1 taken transverse to the elongations showing the respective layers within the parallel plate element 12. Dielectric strip 13 is intermediate conductive foils 14a and 14b. Inner conductive surfaces 14c and 14d, of 14a and 14b respectively, are held in parallel arrangement with the dielectric strip 13 by the adhesive layers 17a and 17b. The capacitance characteristics of the parallel plate element is readily visible in the laminated arrangement of FIG. 2. The distance between conductive surfaces 14c and 14d correspond to the distance between conducting surfaces in a parallel plate capacitor. The capacitive dielectric is composed of the dielectric strip 13 and the adhesive layers 17a and 17b.

It is well known that the capacitance, C, for such a parallel plate capacitor is calculated by the formula $C = KeA/D$, where K is the dielectric constant, e is the permittivity constant, A is the surface area of one of the conductive surfaces and D is the distance between the parallel plates. If the electrical element is constructed as shown in FIG. 2 with uniform cross section throughout its length, then the equation for capacitance becomes $C = (KeW/D)L$ wherein W is the width of the conductive surface and L is the length of the conductive surface. While any value of capacitance can be used values in the range of 1 to 100 picofarads per inch are easily obtainable. Some installations may use such elements having much larger electrical capacitance per inch. Depending upon the length of the solid being monitored and the magnitude of the break or fracture desired to be detected, larger elements and corresponding larger capacitance could be used. In mining installations a convenient size element can be made using conductive foil less than 5 mil thick and less than one and one half inches wide, with a dielectric of similar thickness and less than two inches wide.

In referring to FIG. 2 is should be noted that in cross-section the dielectric strip 13 has a larger width than the respective conductive foil 41a and 14b. The wider dielectric strip in this embodiment acts as a protective barrier between the respective conducting surfaces 14a and 14d. In a one inch wide dielectric strip is used with one half inch wide conductive foils centered on the dielectric, a one quarter inch barrier exists to prevent the foils from shorting together along each edge of the element.

It has been found that 3 mil hard aluminum foils as the conductive foils, and 3 mil paper tape as the dielectric strip with a 1 mil adhesive layer, produces a parallel plate element having good flexibility during insertion into the borehole and such strip is easily sheared by disturbances in the solid, for example earth disturbances in mining installations.

FIG. 3 shows a cross-section of another embodiment in which a parallel plate arrangement is encased in an outer insulation. The dielectric slab 51 is intermediate the two conductive plates 52a and 52b. An outer insulation covering 53 has been added. Such an insulation can be used to add additional rigidity to the element and/or simultaneously to protect the element from intrusion of water, acid, gas or other foreign materials. The element shown in FIG. 3 has a capacitance that can be calculated by the same equation as given for the element in FIG. 2.

FIG. 3 is one example of an element that does not use an adhesive to maintain the proper spacing between the conductive means such as plates or foils for example. The adhesive layers may be omitted if the conductive means is bonded directly on the dielectric such as when a conductive metal coating is used as the conductive means. In some embodiments the dielectric itself is the adhesive as when the conductive foil is attached to a plastic dielectric, for example.

Referring now to FIG. 4 there is shown a cross-section of an element having a coaxial arrangement. The coaxial element is composed of a center conductor 56 having a circular outer conducting surface 56a. Coaxially surrounding the center conductor 56 is a dielectric tube 57 having uniform wall thickness. Concentric with the dielectric tube is outer conductor sleeve 58 having an inner conducting surface 58a. The element is then encased in an outer protective covering 59. The protective covering could be omitted if the outer conductor 58 is made sufficiently durable for the specific application. While the embodiment shown in FIG. 4 does not have an adhesive layer shown, such a layer could be used.

If the coaxial element has a uniform cross section throughout its length, then its capacitance will be a linear function of the length of the element. Such a coaxial element has a capacitance given by the equation $C = 2\pi KeL/\ln(a/b)$. Where a is the radius of the inner conductor; and L is the total length of one of the conductive surfaces; and b is the distance from the center of the inner conductor to the inner surface of the outer conductor; and K is the dielectric constant; and e is the permittivity constant.

Similar to the element shown in FIG. 1 a coaxial element can have the conductive means or one end shorted so as to allow for a continuity check prior to capacitance measuring. This can be done by electrically connecting one end of the center conductor 56 to an adjacent surface on the outer conductor 58.

While two specific types of elongated elements, parallel plate and coaxial, have been described it is to be understood that elements composed of variations of these or other known types of capacitor design are included within the scope of this invention. Such other embodiments would include elements wherein at least one of the conducting surfaces is a rigid support member such as for example an anchoring or roof bolt. In such systems only one of the conducting means in the element need be frangible or easily shearable. Depending upon the desired accuracy and dimensions some applications may use the actual grout material itself as a dielectric between two conducting surfaces.

While an equation for the capacitance, such as the two stated previously, can be determined for any given geometric structure by an analysis of electric fields using Gauss's law. Such equations are not necessary to determine the capacitance as a function of length of the elongation as empirical methods can be used. After any element has been formed having uniform cross-sectional dimensions and materials, such an element will have a capacitance which is a linear function of the length of the elongation. Using instrumentation the capacitance of the complete element can be measured; such measurement may be taken after the element is inserted into the solid and prior to any disturbance. This measured total capacitance divided by the total length is a constant u. For linear varying capacitance this relationship can be written as $C = F(x) = ux$, where x is the length of an element.

Since the constant u is the same before and after the break, this equation can be used to solve for the value of x after the break by dividing the capacitance measured after the break by the constant u. The new value for x will indicate the length of the element after the break.

While any dielectric material can be used it may be desirable in some applications to use a highly breakable dielectric such as glass. Generally a somewhat flexible dielectric such as paper or plastic will result in easy storage prior to insertion of the element into a borehole. The use of materials such as aluminum foil, and plastic tape allow for easy transportation and cutting of laminated materials to the exact length at the insertion site during grouting operations.

FIG. 5 shows a cross-section of an installation of a parallel plate element firmly embedded in a grout filled borehole. The borehole 21 is drilled into the face 26 of an earth formation 20. A parallel plate element 12 is inserted into the borehole 21 so that the element 21 extends generally axially within the borehole 21. When the element is in proper position the hole is next filled with the grout material 22, such as for example, concrete. The embodiment shown in FIG. 5 has provision for the borehole to be filled with grout material 22 by means of hollow grout pipe 24. A seal plug 27 is fitted into the mouth of the borehole and has provision for the grout pipe 24 and the connector 25 to extend through the seal plug 27.

While many means can be used to provide electrical connection from the element 12 to a position outside the borehole at the face 26, the embodiment in FIG. 5 uses electrical connections 23a and 23b which are in electrical contact with the respective conductive foils of 14a and 14b and the grout pipe 24 and connector rod 25. When so connected an electrical current path exists through the series arrangement of grout pipe 24, electrical connection 23a, conductive foil 14a, shorting fold 16, conductive fold 14b, electrical connection 23b and connector rod 25.

If a continuity detector is connected to the grout pipe 24 and the connector rod 25 as shown in FIG. 5, such continuity detector will show a very low resistance in the current path. This low resistance indicates that the element 12 is intact and no disturbance of the earth has occurred. In normal testing it would not be necessary to take further capacitive measurements; embodiment not using shorting fold 16 would indicate the total capacitance C, corresponding to an element of length L.

The total capacitance, C of the element 12 is known either from calculation or from actual measurement prior to any break of the element. If an element having its capacitance varying as a linear function of length such as in FIG. 5 is used, then the capacitance per unit length, u, is C/L.

FIG. 5 shows a typical installation with an element length L where the element is set back or recessed a distance S from the face 26. While the scope of this invention encompasses any distance L, experimentation has been done in which L varied from a few feet to several hundred feet. In installations where L is several hundred feet or where accuracy is not critical the dimension S may be neglected in calculating the position of a break. In other installations the end of the element 12 may be extended to the face so that the set back dimension S is zero.

The installation shown in FIG. 5 is in a vertical borehole having an open bottom. Such an installation would be typical of a mine roof bolt hole. Other installation sites would include for example horizontal boreholes, vertical top opening holes, and cast concrete structures.

Referring to FIG. 6, this shows the installation of FIG. 5 after a disturbance has occurred in the earth formation. The displaced earth 20b has caused the grout material to separate into three sections, a severed grout 22a, a displaced grout 22b and a remaining grout 22c. The displaced grout 22b has caused the element 12 to break into three portions. A portion of the element 12b has become displaced and severed; and a portion 12a has become severed. The remaining portion 12c is intact and electrically connected to the connector rod 25 and grout pipe 24. Because the severed element 12a containing the shorting fold 16, is no longer in electrical connection with the conductive foils of element portion 12c, a complete current path does not exist between the grout pipe 24 and connector rod 25. When an ohmeter or other means for indicating continuity means is attached to the grout pipe 24 and connector rod 25, an open circuit is indicated by the high resistance measured. The continuity detector could be any known circuit such as for example, a lamp or voltage source in series, or an ammeter and battery in series. In normal installations a simple continuity test can be made to detect disturbances as a prerequisite to the more exacting capacitance measurement. A series of such elements may be electrically interconnecting so that an automatic monitor of continuity could indicate a disturbance in the system.

To determine the position of the break in element 12 of FIG. 6 a capacitance measuring instrument is connected to the connector rod 25 and the grout pipe 24. The capacitance measured after an earth disturbance or fault, herein referred to as the break capacitance, is related to the length of the element portion 12c by the same function as previously calculated or measured for the unbroken element 12. The distance B can be found by substituting into that equation the break capacitance and solving for the length of the element which corresponds to B in FIG. 6. The sum of S and B will correspond to the position of the break.

While the earth movement in FIG. 6 has resulted in a single stratified movement of earth 20b, actual earth disturbances may cause additional movements or be of such magnitude so as to displace both section 12a and 12b of the element. The procedure previously described allows position determination of the disturbance in closest proximity to the face 26. Should the installation allow additional electrical connectors to the end of the element opposite the face such as on portion 12a in lieu of the shorting fold 16, then the position of the break area could be ascertained relative to both ends of the element by using the measured break capacitances of both portions 12a and 12c. Such additional electrical connector would be brought out of the solid in a direction opposite the face 26, so as not to be affected by the disturbance. Such additional connection would allow the portion 12a to be measured in the same way as 12c. These additional electrical connections can be brought to the face 26 or another measuring position in any manner such that they do not electrically disconnect during a disturbance.

In the preferred embodiments specifically described the position of the disturbance is indicated by a reduction in the measured capacitance of the element. This reduction occurs when at least one of the conductive surfaces of the element is severed. In the drawings, both conductive foils and surfaces, and the dielectric have been shown as severed, but it is to be understood that only one surface need be broken to indicate the position of a disturbance. For this reason it may be desirable, where fine sensitivity is required to have one conductive surface made of a thin conducting metal coating which is easily broken.

FIG. 7 shows a block diagram for a disturbance tester connected to an element similar to FIG. 6 after a break has occurred. The tester uses a switch or mode selector 43 to electrically connect one of three circuits to the elements by means of connections 23a and 23b. The element having original length L is shown severed having a remaining length B. The element is composed of a dielectric slab 13 intermediate two conductive foils 14a and 14b. At the end of the element opposite the electrical connections 23a and 23b is a shorting fold 16.

Prior to the fault the capacitance and length of the element have been determined and recorded. In the normal sequence of operations the tester is periodically connected to the element preferably keeping all leads relatively short to avoid stray capacitance. The mode selector is placed in position "a" so as to connect the continuity detector 40 to the element. The detector 40 may be any known means for continuity indication such as for example an ohmeter. If the element is unbroken, a low resistance current path exists between conducting foils 14a and 14b through the shorting fold 16. If as shown in FIG. 7 the element is broken the detector 40 will show a high resistance path or open circuit indicating an earth disturbance.

If the detector 40 indicates an open circuit the operator changes the mode selector 43 to position "b" thereby connecting a capacitance measuring device 41 to the element. The capacitance measuring device can be of any known type and for ease of operation can be calibrated so that it reads directly in units of length. If the capacitance measuring device reads in units of capacitance, the length B can be calculated by the equation previously given.

In some environments, especially where moisture is present, the dielectric strip 13 may develop leakage current paths, represented in FIG. 7 as RL. This leakage path shown as a leakage resistance RL, is often present when a moisture absorbant material such as paper is used for the dielectric. Leakage resistance should generally be larger than 20,000 ohms to facilitate accurate capacitance readings from measuring device 41. If the leakage resistance is low, indicating sizable current paths between conductive foils 14a and 14b, an electrical heating power source 42 may be connected to the element by position "c" on the mode selector 43. This source 42 provides current to produce $I^2R$, resistance heating within the element.

Figure 8A:
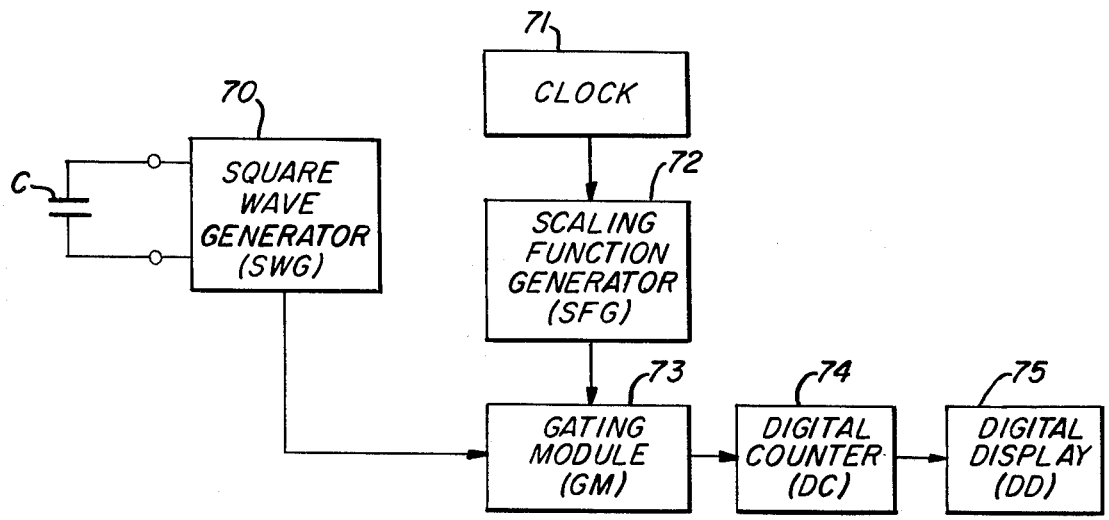
FIG. 8a is a block diagram of a circuit to measure the capacitance of the element.

FIG. 8a is a block diagram of a circuit for a capacitance measuring device which can be used as the device 41 in FIG. 7. The square wave generator or SWG 70 in the form shown is of the type with an output frequency which is a function of the connected capacitance C. The output pulses of the SWG 70 are used to trigger a gating module GM, reference numeral, 73. The period of the output of SWG 70 is a known function, usually linear, of the capacitance C. This period is used as the "on" interval for the GM 73. The clock, 71 feeds a series of pulses to the scaling function generator or SFG 72 which scales the frequency so that the readout will be in proper engineering units of length. The output of the SFG 72 is permitted to pass through the gating module 73 during a period of the SWG. This string of pulses is proportional to C and are counted on the digital counter or DC 74. This count can then be shown on the digit display or DD 75. The actual circuits used in each of the blocks 71 through 75 are well known in the art and a variety of known circuits can be used for any of the circuits represented by the blocks.

The circuit diagram shown in 8b is an example of an embodiment of a capacitance measuring device which compares the output of two matched monostable multivibrators. The output of one monostable multivibrator MSMV-1, 81, is a fixed pulse having width T. The output of the other monostable multivibrator MSMV-2, 82, is a pulse having a width T+t where t is proportional to the capacitance C added in the external circuit. The values for C1 and R2 are fixed and may be chosen so as to enhance the relation of T to t so that desired accuracy can be achieved. While R1 will normally be equal to R2, R1 may be variable so as to provide a calibration.

Figure 8B:
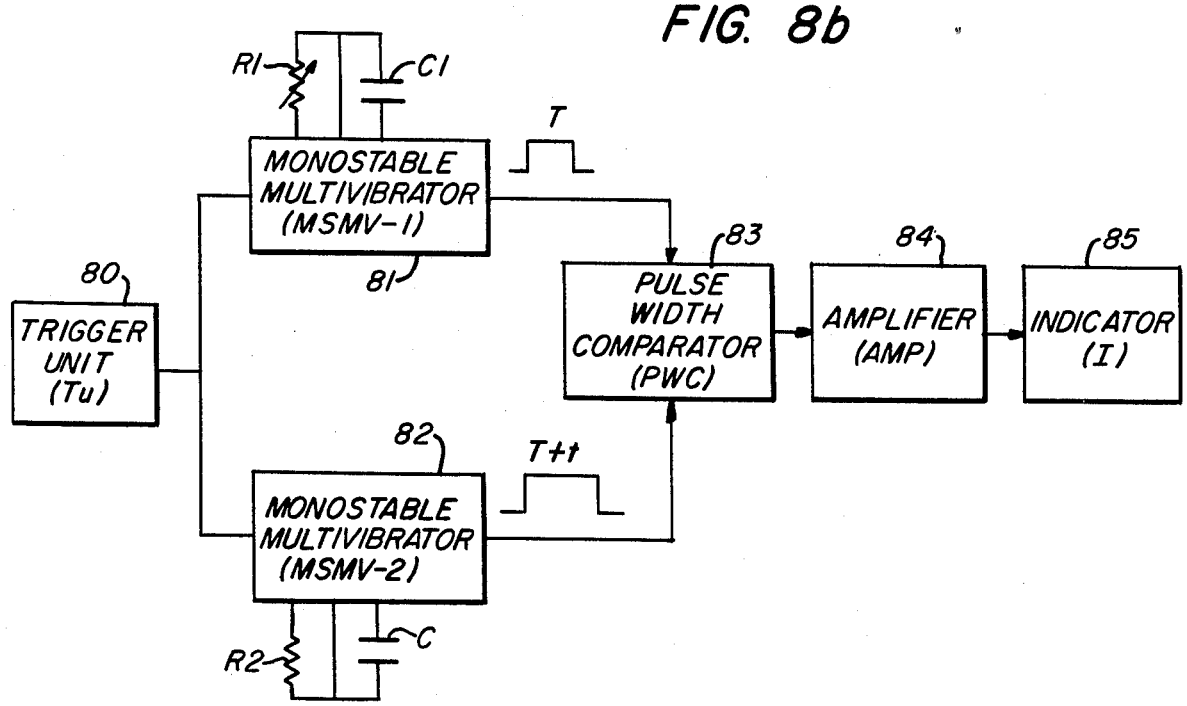
FIG. 8b is a block diagram of a circuit used to measure the capacitance of the element using two monostable vibrators.

Both MSMV-1, 81 and MSMV-2, 82 are initiated simultaneously by the triggering unit or Tu, 80. The output pulses, as shown on FIG. 8b are fed to a pulse width comparator or PWC, 83. The PWC subtracts the output from MSMV-1 from the output of MSMV-2 and feeds the remaining signal to the amplifier or AMP, 84.

The AMP, 84 amplifies the signal t which is proportional to C. The signal can also be scaled by the amplifier so that when it is fed into the indicator or I, 85, the units will read directly in units of length. If for example, I is a meter it can be calibrated to read in feet, meters or other units of length. The individual blocks of FIG. 8b are well known to those skilled in the art. While any capacitance measuring device can be used; it is desirable that the device be designed to operate accurately even when a leakage resistance is present.

Figure 8C:
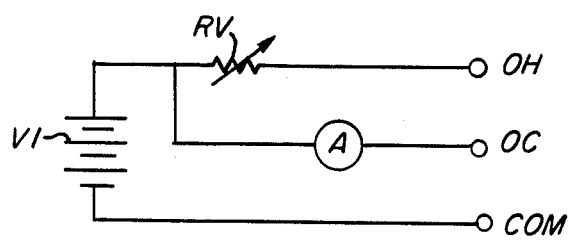
FIG. 8c is a diagram of a circuit which may be used to detect continuity and provide variable heating current.

Referring now to FIG. 8c, which shows a circuit that can be used both as the continuity detector 40 and the heating power source 42. When the terminals OC and COM are used the battery V1 and the ammeter A are in series to function as an ohmmeter and a means for indicating continuity. If the terminals OH and COM are used the circuit can function as a heating current source with the battery V1 and the variable resistance RV in series.

While the specification has shown and described certain present preferred embodiments it is to be distinctly understood that the invention is not limited thereto but may be embodied in other alternatives, modifications and variations apparent to those skilled in the art. Accordingly, it is intended to embrace all such alternatives, modifications, and variations as fall within the spirit and scope of the appended claims.

What is claimed is:

1. An apparatus for determining the position of a structural break in a solid formation comprising:
   a continuous, elongated, linearly extending electrical element adapted to be embedded in solid formation, said element comprising;
   two flat continuous, elongated, linearly extending frangible conductive tape means for conducting an electric current and storing an electric charge and adapted to be connected to a capacitance measuring instrument;
   a flat continuous, elongated, linearly extending dielectric paper tape disposed intermediate said two flat continuous, elongated, linearly extending frangible conductive tape means with one said flat continuous, elongated, linearly extending frangible conductive tape means abutting the first surface of said flat continuous, elongated, linearly extending flexible dielectric paper tape along said flat continuous, elongated, linearly extending flexible dielectric paper tape length and another said flat continuous, elongated, linearly extending frangible conductive tape means abutting the second surface of said flat continuous, elongated, linearly extending flexible dielectric paper tape along said flat continuous, elongated, linearly extending flexible dielectric paper tape length whereby the electrical capacitance formed between said two flat continuous, elongated, linearly extending frangible conductive tape means is a function of the length of said flat continuous, elongated, linearly extending frangible conductive tape means and;
   grouting means surrounding said electrical element rigidly embedding said electrical element in such solid formation, whereby a fracture in said grouting means due to structural break in the solid formation causes a severing of said flat continuous, elongated, linearly extending frangible conductive tape means in close proximity to said fracture and wherein the location at which said severing occurs may be determined by the capacitance measured between said two flat continuous, elongated, linearly extending frangible conductive tape means by said capacitance measuring means.

2. An apparatus of claim 1 wherein said flat continuous, elongated, linearly extending frangible conductive tape means and said flat continuous, elongated, linearly extending flexible dielectric paper tape are generally of uniform cross section throughout their length, whereby the capacitance formed is a linear function of the length of said flat continuous, elongated, linearly extending frangible conductive tape means.

3. The apparatus of claim 1 wherein said two flat continuous, elongated, linearly extending frangible conductive tape means are electrically connected at one end of said flat continuous, elongated, linearly extending flexible dielectric paper tape to form one conductive path.

4. An apparatus of claim 1 wherein a cross section taken transverse to the maximum dimension of said flat continuous, elongated, linearly extending flexible dielectric paper tape has a maximum cross sectional dimension greater than the maximum cross sectional dimension of said two flat continuous, elongated, linearly extending frangible conductive tape means.

5. The apparatus of claim 1 wherein said apparatus has superimposed thereupon an exterior nonconductive material.

6. An apparatus of claim 1 wherein said flat continuous, elongated, linearly extending flexible dielectric paper tape comprises a tape less than two inches in width and less than five thousandths of an inch thick; and said two flat continuous, elongated linearly extending frangible conductive tape means comprises an aluminum tape less than one and one-half inches wide and less than five thousandths of an inch thick.

7. An apparatus as described in claim 1 which further comprises connective means for electrical connection to each of said flat continuous, elongated, linearly extending frangible conductive tape means at one end of said apparatus and capacitance measuring means for determining the electrical capacitance of said flat continuous, elongated, linearly extending conductive tape means by contacting said connective means.

8. The apparatus of claim 7 further comprising shorting means for electrical connection between said flat continuous, elongated, linearly extending frangible conductive tape means on the end of said apparatus opposite from said connective means.

9. The apparatus of claim 8 further comprising continuity check means operatively associated with said connective means for indicating the continuity of the series arrangement of said shorting means and said two flat continuous, elongated, linearly extending frangible conductive tape means.

10. The apparatus of claim 9 further comprising resistance measuring means for determining the electrical resistance between said two flat continuous, elongated, linearly extending frangible conductive tape means.

11. An apparatus of claim 9 further comprising drying means for applying an electric current to said two flat continuous, elongated, linearly extending frangible conductive tape means whereby causing a resistance heating element in said flat continuous, elongated, linearly extending flexible dielectric paper tape.

* * * * *